(12) United States Patent
Sorin et al.

(10) Patent No.: US 11,474,099 B2
(45) Date of Patent: Oct. 18, 2022

(54) METHOD FOR DIAGNOSING THE SULPHUR NUTRITION STATE OF A PLANT

(71) Applicants: Agro Innovation International, Saint Malo (FR); Universite de Caen Basse Normandie, Caen (FR)

(72) Inventors: Elise Sorin, Sees (FR); Mustapha Arkoun, Saint-Malo (FR); Florence Cruz, Saint-Malo (FR); Jean-Claude Yvin, Saint-Malo (FR); Anne Maillard, Rennes (FR); Sylvain Diquelou, Douvres la Delivrande (FR); Philippe Etienne, Caen (FR); Alain Ourry, Aunay sur Odon (FR)

(73) Assignees: AGRO INNOVATION INTERNATIONAL, Saint-Malo (FR); UNIVERSITE DE CAEN BASSE NORMANDIE, Caen (FR)

( * ) Notice: Subject to any disclaimer, the term of this patent is extended or adjusted under 35 U.S.C. 154(b) by 1109 days.

(21) Appl. No.: 16/074,236

(22) PCT Filed: Feb. 3, 2017

(86) PCT No.: PCT/FR2017/050248
§ 371 (c)(1),
(2) Date: Jul. 31, 2018

(87) PCT Pub. No.: WO2017/134400
PCT Pub. Date: Aug. 10, 2017

(65) Prior Publication Data
US 2019/0339259 A1 Nov. 7, 2019

(30) Foreign Application Priority Data
Feb. 4, 2016 (FR) ...................... 1650890

(51) Int. Cl.
*G01N 33/68* (2006.01)
*G01N 33/28* (2006.01)
*G01N 33/50* (2006.01)
*G01N 23/223* (2006.01)
*G01N 21/64* (2006.01)
(Continued)

(52) U.S. Cl.
CPC ......... *G01N 33/5097* (2013.01); *G01N 21/64* (2013.01); *G01N 23/223* (2013.01); *G01N 30/72* (2013.01); *G01N 33/0098* (2013.01); *G01N 33/287* (2013.01); *G01N 33/6848* (2013.01)

(58) Field of Classification Search
CPC .. G01N 33/6848; G01N 33/287; G01N 21/64; G01N 33/5097; G01N 23/223; G01N 30/72; G01N 33/0098
USPC .................................................. 436/83, 123
See application file for complete search history.

(56) References Cited

FOREIGN PATENT DOCUMENTS

| CN | 103141515 A | 6/2013 |
|----|-------------|--------|
| CN | 105237084 A | 1/2016 |

OTHER PUBLICATIONS

Spencer, K. et al, Agronomy Journal 1980, 72, 469-472.*
(Continued)

*Primary Examiner* — Arlen Soderquist
(74) *Attorney, Agent, or Firm* — MH2 Technology Law Group, LLP

(57) ABSTRACT

The invention relates to a novel method for diagnosing the sulfur nutrition state of a plant by measuring the content of certain mineral nutrients in the leaves.

21 Claims, 7 Drawing Sheets

Figure 1:
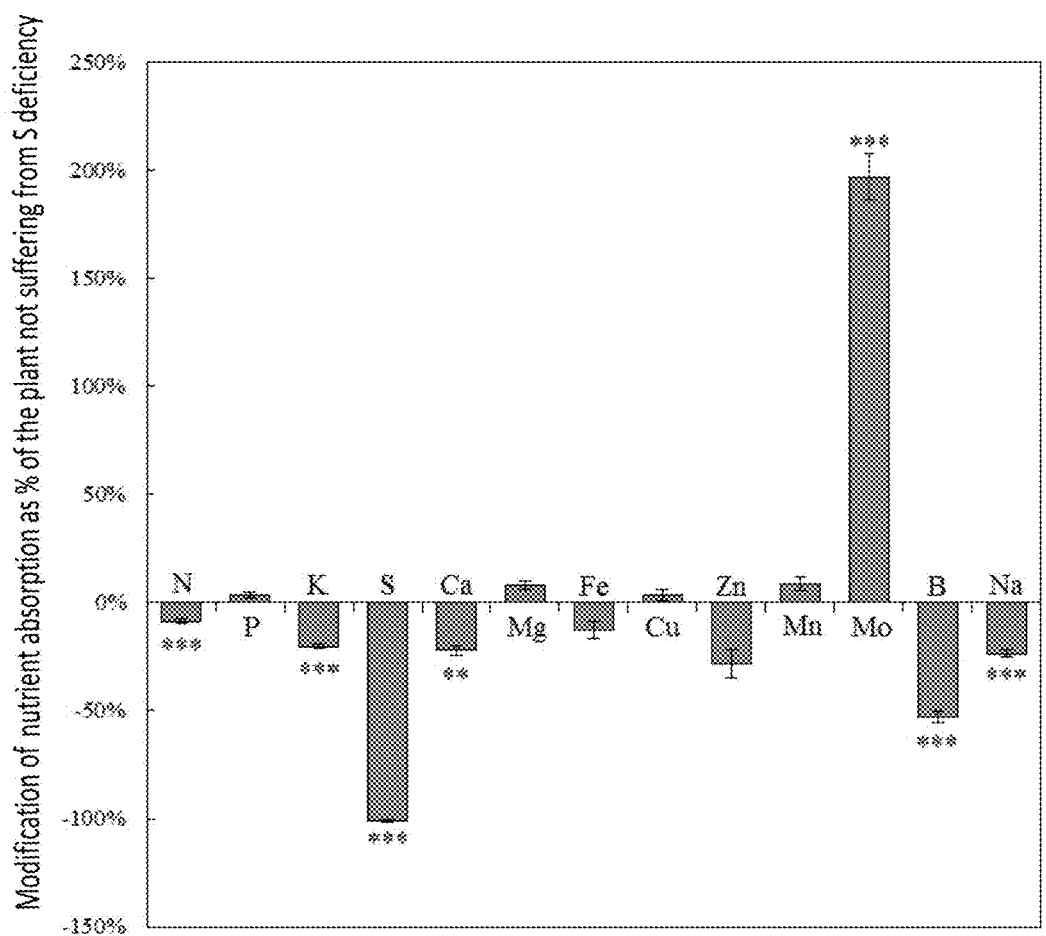

(51) Int. Cl.
*G01N 30/72* (2006.01)
*G01N 33/00* (2006.01)

(56) References Cited

OTHER PUBLICATIONS

Bush, L. P. et al, Canadian Journal of Botany 1981, 59, 536-541.*
Elwali, A. M. O. et al, Agronomy Journal 1984, 76, 466-470.*
Kanwar, J. S. et al, in "Fertilizer sulfur and food production" 1986, 51-90.*
Jones, M. B. et al, California Agriculture 1986, 19-21.*
Johnson, G. V. et al, in "Soil Testing and Plant Analysis" vol. 3, 3rd Ed,Westerman, R. Ed, 1990, 265-273.*
Lewis, D. C. et al, Australian Journal of Experimental Agriculture 1993, 33, 1053-1066.*
Sairam, R. K. et al, Journal of Plant Nutrition 1995, 18, 2093-2103.*
Blake-Kalff, M. M. A. et al, Plant and Soil 2000, 225, 95-107.*
Kelling, K. A. et al., Fertilizer Dealer Meetings 2000, 11 pages, downloaded from https://soilsextension.qa.webhosting.cals.wisc.edu/wp-content/uploads/sites/68/2014/02/Plant-Analysis-as-Tool.pdf.*
Randall, P. J. et al, Nutrient Cycling in Agroecosystems 2003, 65, 211-219.*
McCray, J. M. et al, Jornal of Agronomy & Crop Science 2010, 196, 66-75.*
Dagbenonbakin, G. D. et al, Scientific Research and Essays 2013, 8, 1562-1569.*
Sorin, E. et al, Journal of Experimental Botany 2015, 66, 6175-6189.*
Reich, M. et al., Frontiers in Plant Science 2016, 7, Article 541, 8 pages.*
Maillard, A. et al, Journal of Experimental Botany 2016, 67, 5631-5641.*
Maillard, A. et al., PLOS One 2016, 10, Article 0166910, 20 pages.*
Alhendawi et al., "Evidence That Sulfur Deficiency Enhances Molybdenum Transport in Xylem Sap of Tomato Plants," Journal of Plant Nutrition, vol. 28, No. 8, pp. 1347-1353, Aug. 2005.
Campbell, "Reference Sufficiency Ranges for Plant Analysis in the Southern Region of the United States," Southern Cooperative Series Bulletin, SCSB #394, Jul. 2000.
Detar et al., "Molybdenum accumlation, tolerance and molybdenum-selenium-sulfur interactions in Astragaluls selenium hyperaccumulator and nonaccumulator species," Journal of Plant Physiology, vol. 183, pp. 32-40, Jul. 2015.
Fitzpatrick et al., "Molybdate transport thorugh the plant sulfate transporter SHST1" FEBS Letters, vol. 582, pp. 1508-1513, Apr. 2008.
Hawkesford, "Plant response to sulphur deficiency and the genetic manipulation of sulphate transporters to improve S-utilization efficiency," Journal of Experimental Botany, vol. 51, No. 342, pp. 131-138, Jan. 2000.
International Search Report issued in application No. PCT/FR2017/050248, dated Apr. 28, 2017.
Kaiser et al., "The Role of Molybdenum in Agricultural Plant Production," vol. 96, pp. 745-754, Mar. 2005.
Mcgrath et al., "Predicting molybdenum toxicity to higher plants: Influence of soil properties," Environmental Pollution, vol. 158, No. 10, pp. 3095-3102, Oct. 2010.
Schiavon et al., "Selenate and molybdate alter sulfate transport and assimilation in *Brassica juncea* L. Czern.: Implications for phytoremediation," Environmental and Experimental Botany, vol. 75, pp. 41-51, Aug. 2011.
Shinmachi et al., "Influence of Sulfur Deficiency on the Expression of Specific Sulfate Transporters and the Distribution of Sulfur, Selenium, and Molybdenum in Wheat," Plant Physiology, vol. 153, No. 1, pp. 327-336, Mar. 2010.

* cited by examiner

METHOD FOR DIAGNOSING THE SULPHUR NUTRITION STATE OF A PLANT

TECHNICAL FIELD

The invention relates to a novel method for diagnosing the sulfur nutrition of a plant by measuring the content of certain mineral nutrients in said plant.

TECHNICAL BACKGROUND

During their development, plants need to maintain a certain level of homeostasis between the various mineral nutrients. Thus, plants must constantly absorb nutrients from the soil by means of a complex network of specific transporters that is present in the roots. Certain mineral nutrients can also be absorbed via non-specific transporters. Consequently, mineral nutrients of different nature can compete at the active site of non-specific transporters. Non-specific systems for absorption of mineral nutrients which are capable of transporting both sodium ions ($Na^+$) and potassium ions ($K^+$) have been identified in the root cells of plants. It has in particular been demonstrated that, when the soil is rich in $Na^+$, plants absorb $Na^+$ rather than $K^+$. Mention may also be made of another case of competition between various nutrient elements present in the rhizosphere, which involves sulfate ($SO_4^{2-}$), molybdate ($MoO_4^{2-}$), selenate ($SeO_4^{2-}$) and tungstate ($WO_4^{2-}$). It has in fact been suggested that molybdate absorption can also take place via sulfate transporters. It has in particular been shown that molybdate and sulfate can compete at the binding site of the same transporters, in particular of sulfate transporters.

Sulfur (S) is an essential element for protein synthesis in plants. S deficiency considerably reduces nitrogen (N) use efficiency and therefore limits protein synthesis. The signs of deficiency comprise in particular yellowing of new leaves or of young organs.

Certain cruciferous plants, such as rapeseed and cabbage, require a large amount of sulfur. They in fact have an additional S requirement in order to ensure the production of glucosinolates, which are used by plants in their mechanism of defense against certain pathogens.

Sulfur-deficient rapeseed can exhibit a purple color and shriveled up young leaves, late and extended flowering, pale-colored flowers and siliques which are smaller and fewer in number. Furthermore, S-deficient rapeseed generates yield losses and seeds which are of poorer quality, through a modification of the lipid and protein composition of the seeds.

Studies have demonstrated an accumulation of certain mineral nutrients, such as molybdenum (Mo) and selenium (Se), in response to an S deficiency. It has been suggested that the decrease in sulfate absorption observed in a situation of S deficiency could be due to the binding of molybdate at the active site of root sulfate transporters, which binding is promoted by sulfate deficiency. It has also been demonstrated that Mo accumulation in a situation of S deficiency correlates with an increase in root sulfate transporter expression. It has also been shown that the addition of sulfur results in a significant decrease in Mo absorption.

Nevertheless, the interactions between the various mineral nutrients necessary for plants are numerous and it is difficult to predict and identify good indicators which make it possible to diagnose the sulfur nutrition state of a plant.

It has in particular been suggested to diagnose S deficiencies by measuring the total S content of the plant or the $SO_4^{2-}$ content or by calculating the nitrogen/sulfur (N/S), malate/sulfate or ($Cl^-+NO_3^-+PO_4^{3-}$)/$SO_4^{2-}$ ratios. However, these parameters can be distorted depending on the developmental stage of the plant or can require laboratory analyses which are difficult to implement, thereby making the use of these parameters relatively unreliable for diagnosing a sulfur deficiency. It is therefore essential to have available a reliable method which is easy to implement for diagnosing the sulfur nutrition state of a plant, in particular for diagnosing a sulfur (S) deficiency.

The applicants have demonstrated that the Mo/S concentration ratio in a leaf sample is a reliable and precise indicator which is easy to implement for diagnosing the sulfur nutrition state of a plant, and thus diagnosing an S deficiency.

SUMMARY OF THE INVENTION

The present invention aims to provide a novel method for diagnosing the sulfur nutrition state of a plant by measuring the content of certain mineral nutrients in a leaf sample.

According to a first aspect, the invention relates to a method for diagnosing the sulfur nutrition state of a plant, comprising the following steps:
a) taking a leaf sample from the plant;
b) measuring the sulfur (S) content of the sample in mg/g;
c) measuring the molybdenum (Mo) content of the sample in µg/g;
d) calculating the Mo/S ratio;
e) comparing with a reference Mo/S ratio of a plant not suffering from sulfur deficiency and/or with a reference Mo/S ratio of a plant suffering from sulfur deficiency; and
f) deducing the sulfur nutrition state of the plant.

According to a second aspect, the invention relates to a method for diagnosing the sulfur nutrition state of a plot, comprising the following steps:
a) taking a leaf sample representative of the plot;
b) measuring the sulfur (S) content of the sample in mg/g;
c) measuring the molybdenum (Mo) content of the sample in µg/g;
d) calculating the Mo/S ratio;
e) comparing with a reference Mo/S ratio of a plot not suffering from sulfur deficiency and/or with a reference Mo/S ratio of a plot suffering from sulfur deficiency; and
f) deducing the sulfur nutrition state of the plot.

According to a third aspect, the invention relates to a method for adjusting the sulfur fertilization of a plant or of a plot, comprising the following successive steps:
A) carrying out the method of diagnosis according to the invention on the plant or the plot;
B) adding a sulfur-containing fertilizer if a sulfur deficiency or a risk of deficiency is detected during step A).

According to a fourth aspect, the invention relates to the use of the foliar Mo/S weight ratio, and optionally of the foliar (Cl+P)/S weight ratio, for determining the sulfur nutrition state of a plant or of a plot.

DETAILED DESCRIPTION OF THE INVENTION

The invention ensues from the surprising advantages, demonstrated by the inventors, of a correlation between the Mo/S ratio of a leaf sample of a plant or of a plot and the sulfur nutrition state of said plant or plot.

The invention in fact relates to a method for diagnosing the sulfur nutrition state of a plant, comprising the following steps:
a) taking a leaf sample from the plant;
b) measuring the sulfur (S) content of the sample in mg/g;
c) measuring the molybdenum (Mo) content of the sample in µg/g;
d) calculating the Mo/S ratio;
e) comparing with a reference Mo/S ratio of a plant not suffering from sulfur deficiency and/or with a reference Mo/S ratio of a plant suffering from sulfur deficiency; and
f) deducing the sulfur nutrition state of the plant.

All plants require mineral nutrients in order to grow optimally, in particular S nutrients. Thus, for the purposes of the invention, the "sulfur nutrition state" is an indicator which makes it possible to know whether the plant has sufficient S to enable optimal growth thereof. An evaluation of the "sulfur nutrition state" is generally based on the conflict between the S provided by the soil (i.e. the sulfur present in the soil) and the S requirement of the plant (i.e. to ensure optimal growth of the plant). Since, given the current state of knowledge, it is difficult to determine the S provided by the soil, the analysis of the plant makes it possible to know whether it has sufficient S to ensure optimal growth thereof. A low S availability can affect the sulfur nutrition state of the plant and can cause a sulfur deficiency.

For the purposes of the invention, the term "deficiency" is intended to mean an absence, an insufficient presence or a lack of assimilability of an essential element, thus preventing optimal growth.

For the purposes of the invention, the term "sulfur deficiency" is intended to mean an absence, an insufficient presence or a lack of assimilability of sulfur, thus preventing optimal growth.

Thus, for the purposes of the invention, the term "plant suffering from sulfur deficiency" is intended to mean a plant which has not assimilated sufficient sulfur to enable optimal growth thereof.

Thus, for the purposes of the invention, the term "plant not suffering from sulfur deficiency" is intended to mean a plant which has assimilated sufficient sulfur to enable optimal growth thereof.

Thus, for the purposes of the invention, the term "plant having a risk of sulfur deficiency" is intended to mean a plant which has not assimilated sufficient sulfur but which appears to have optimal growth.

A plant or a plot having a risk of sulfur deficiency which has not been treated with a sulfur-containing fertilizer can progress to a plant or a plot suffering from sulfur deficiency. Thus, a major advantage of the present invention is that it makes it possible to deduce whether the plant or the plot is suffering from sulfur deficiency, whether the plant or the plot is not suffering from sulfur deficiency, but also whether the plant or the plot has a risk of sulfur deficiency. This complete diagnosis of the sulfur nutrition state of the plant is one of the advantages of the present invention.

The sulfur nutrition state of a plant is evaluated by taking a leaf sample from the plant. One of the advantages of the present invention is that all types of leaves and leaves at all developmental stages can be used for carrying out the invention.

In one particular embodiment, the plant has been cultivated in an open field.

The method of diagnosis can also be carried out on the scale of a plot, that is to say on the scale of a field all in one piece of the same crop. Thus, the invention is also directed toward a method for diagnosing the sulfur nutrition state of a plot, comprising the following steps:
a) taking a leaf sample representative of the plot;
b) measuring the sulfur (S) content of the sample in mg/g;
c) measuring the molybdenum (Mo) content of the sample in µg/g;
d) calculating the Mo/S ratio;
e) comparison with a reference Mo/S ratio of a plot not suffering from sulfur deficiency and/or with a reference Mo/S ratio of a plot suffering from sulfur deficiency; and
f) deducing the sulfur nutrition state of the plot.

In this embodiment, the leaf sample representative of the plot can be taken from a single plant or from several plants. Preferably, the leaf sample representative of the plot comprises leaves originating from several distinct plants present on the plot, advantageously present at various places on the plot.

Preparation of the Sample

The leaf sample can be prepared in various ways in order to be able to measure the content of mineral nutrients of interest.

In one particular embodiment, steps b) and c) are directly carried out on a dried leaf sample which is taken directly in the soil or on the plant. The measurement then takes only a few minutes, in particular by X-ray fluorescence spectrometry or by inductively coupled plasma mass spectrometry (e.g. for Mo contents of less than 10 ppm).

In one particular embodiment, the leaf sample is dried and ground before steps b) and c), it being understood that the leaf sample can only be ground if the leaf sample is already dry, for example if it is a dried leaf sample which is taken directly in the soil or on the plant.

The leaf sample can be dried by methods well known to those skilled in the art, such as for example drying in an oven or in a microwave oven, advantageously by freeze-drying. A sample is considered to be dried when it contains less than 5% of water, advantageously less than 3% of water.

The sample can be ground by methods well known to those skilled in the art and easy to carry out, such as for example with a coffee grinder or advantageously with a ball mill.

Generally, the leaf sample comprises between 40 mg and 50 g of leaf solids, for example between 50 mg and 50 g, between 500 mg and 50 g, between 1 g and 50 g, between 1 g and 10 g, or else between 10 g and 50 g of leaf solids.

Measurement of the Mineral Nutrient Content

The measurement of the content of mineral nutrients of interest (i.e. S and Mo, and optionally Cl and P) is carried out by an appropriate analysis method. Various known methods of analysis make it possible to measure the mineral nutrient content of a leaf sample, such as for example X-ray fluorescence spectrometry (for the analysis of S, Cl, P and concentrations of Mo greater than 10 ppm) or plasma mass spectrometry (for the analysis of S, P and concentrations of Mo of less than 10 ppm).

The measurement of the S, Mo, Cl and P content is a weight content:
the sulfur (S) content of the sample is expressed in mg/g, which corresponds to the weight of S expressed in mg contained in 1 gram of dried sample;
the molybdenum (Mo) content of the sample is expressed in µg/g, which corresponds to the weight of Mo expressed in µg contained in 1 gram of dried sample;
the chlorine (Cl) content of the sample is expressed in mg/g, which corresponds to the weight of Cl expressed in mg contained in 1 gram of dried sample;

the phosphorus (P) content of the sample is expressed in mg/g, which corresponds to the weight of P expressed in mg contained in 1 gram of dried sample.

In one particular embodiment, steps b) and c) are carried out by X-ray fluorescence spectrometry or by plasma mass spectrometry.

In one particular embodiment, steps b) and c) are carried out simultaneously. That is to say that the measurement of the S content, optionally chlorine (Cl) and phosphorus (P) content, and the measurement of the Mo content are carried out simultaneously. This embodiment has the advantage of enabling the mineral nutrient content of the same leaf sample to be measured.

Once the measurement of the content of mineral nutrients of interest has been carried out, the Mo/S ratio can be easily calculated.

Comparison with a Reference Ratio

The Mo/S ratio is then compared with a reference Mo/S ratio of a plant or of a plot not suffering from S deficiency and/or a reference Mo/S ratio of a plant or of a plot suffering from S deficiency.

For the purposes of the invention, the expression "reference Mo/S ratio of a plant or of a plot not suffering from S deficiency" is intended to mean the Mo/S ratio of a leaf sample from a plant or from a plot not suffering from sulfur deficiency. The reference Mo/S ratio of a plant or of a plot not suffering from S deficiency can be determined by large-scale studies on plants of which the S nourishment is sufficient to allow the plant to have optimal growth.

For the purposes of the invention, the expression "reference Mo/S ratio of a plant or of a plot suffering from S deficiency" is intended to mean the Mo/S ratio of a leaf sample from a plant or from a plot suffering from sulfur deficiency. The reference Mo/S ratio of a plant or of a plot suffering from S deficiency can be determined by large-scale studies on plants of which the nourishment is substantially devoid of S.

In one particular embodiment, the reference Mo/S ratio of a plant or of a plot not suffering from S deficiency corresponds to the upper threshold of the confidence interval (advantageously for a probability of less than P=0.05 according to the Student's test) of the mean of the Mo/S ratios measured during large-scale studies on plants or plots not suffering from S deficiency. The reference Mo/S ratio of a plant or of a plot suffering from S deficiency corresponds to the lower threshold of the confidence interval (advantageously for a probability of less than P=0.05 according to the Student's test) of the mean of the Mo/S ratios measured during large-scale tests on plants or plots suffering from S deficiency.

These studies make it possible to determine the reference Mo/S ratios for various plant species. It is then possible to constitute a database with the reference Mo/S ratios of various plant species. Such a database can then be used for carrying out the invention, in particular during step e).

It is then possible to determine, for each plant species, a reference ratio above which the plant is considered to be suffering from S deficiency (i.e. above the reference Mo/S ratio of a plant suffering from S deficiency), and a reference ratio below which the plant is considered to be not suffering from S deficiency (i.e. below the reference Mo/S ratio of a plant not suffering from S deficiency). It is therefore possible to determine 3 different sulfur nutrition states for a plant or a plot:

plant or plot not suffering from S deficiency: when the Mo/S ratio of the leaf sample is less than the reference Mo/S ratio of a plant or of a plot not suffering from S deficiency;

plant or plot suffering from S deficiency: when the Mo/S ratio of the leaf sample is greater than the reference Mo/S ratio of a plant or of a plot suffering from S deficiency; and plant or plot having a risk of S deficiency: when the Mo/S ratio of the leaf sample is less than the reference Mo/S ratio of a plant or of a plot suffering from S deficiency and greater than the reference Mo/S ratio of a plant or of a plot not suffering from S deficiency.

In one preferred embodiment, the plant analyzed for its sulfur nutrition state is from the same species as the plant not suffering from sulfur deficiency and/or as the plant suffering from sulfur deficiency (i.e. the plants of step e)). In one preferred embodiment, the plot analyzed for its sulfur nutrition state is from the same species as the plot not suffering from sulfur deficiency and/or as the plot suffering from sulfur deficiency (i.e. the plots of step e)), that is to say that the plants which constitute the plot analyzed for its sulfur nutrition state are from the same species as the plants which constitute the plot not suffering from sulfur deficiency and/or as the plants which constitute the plot suffering from sulfur deficiency.

For example, for rapeseed (*B. napus*):
a plant or a plot is suffering from sulfur deficiency when the Mo/S ratio is greater than 0.28±0.05,
a plant or a plot is not suffering from S deficiency when the Mo/S ratio is less than 0.16±0.05,
a plant or a plot has a risk of sulfur deficiency when the Mo/S ratio is between 0.28±0.05 and 0.16±0.05. The applicants have shown that the Mo/S ratio of a leaf sample from a plant suffering from S deficiency or from a plot suffering from S deficiency was significantly greater than the reference Mo/S ratio of a plant or of a plot not suffering from S deficiency. Thus, the method according to the invention makes it possible to easily diagnose, with accuracy, the sulfur nutrition state of a plant or of a plot.

In one particular embodiment, the plant or the plot (i.e. the plant analyzed or the plot analyzed) is suffering from sulfur deficiency and the Mo/S ratio of the leaf sample is greater than the reference Mo/S ratio of a plant or of a plot suffering from sulfur deficiency.

In another particular embodiment, the plant or the plot (i.e. the plant analyzed or the plot analyzed) is not suffering from sulfur deficiency and the Mo/S ratio of the leaf sample is less than the reference Mo/S ratio of a plant or of a plot not suffering from sulfur deficiency.

In another particular embodiment, the plant or the plot (i.e. the plant analyzed or the plot analyzed) has a risk of sulfur deficiency and the Mo/S ratio of the leaf sample is less than the reference Mo/S ratio of a plant or of a plot not suffering from sulfur deficiency, and the Mo/S ratio of the leaf sample is greater than the reference Mo/S ratio of a plant or of a plot not suffering from sulfur deficiency.

Calculation of the Mo/S and (Cl+P)/S Ratios

In one particular embodiment:
step b) also comprises measuring the chlorine (Cl) and phosphorus (P) content of the sample in mg/g,
step d) also comprises calculating the (Cl+P)/S ratio, and
step e) also comprises comparing with a reference (Cl+P)/S ratio of a plant or of a plot not suffering from sulfur deficiency and/or with a reference (Cl+P)/S ratio of a plant or of a plot suffering from sulfur deficiency.

For the purposes of the invention, the expression "reference (Cl+P)/S ratio of a plant or of a plot not suffering from S deficiency" is intended to mean the (Cl+P)/S ratio of a leaf sample from a plant or from a plot not suffering from sulfur deficiency. The reference (Cl+P)/S ratio of a plant or of a plot not suffering from S deficiency can be determined by large-scale studies on plants of which the S nourishment is sufficient to allow the plant to have optimal growth.

For the purposes of the invention, the expression "reference (Cl+P)/S ratio of a plant or of a plot suffering from S deficiency" is intended to mean the (Cl+P)/S ratio of a leaf sample from a plant or from a plot suffering from sulfur deficiency. The reference (Cl+P)/S ratio of a plant or of a plot suffering from S deficiency can be determined by large-scale studies on plants of which the nourishment is substantially devoid of S.

In one particular embodiment, the reference (Cl+P)/S ratio of a plant or of a plot not suffering from S deficiency corresponds to the upper threshold of the confidence interval (advantageously for a probability of less than $P=0.05$ according to the Student's test) of the mean of the (Cl+P)/S ratios measured during large-scale studies on plants or plots not suffering from S deficiency. The reference (Cl+P)/S ratio of a plant or of a plot suffering from S deficiency corresponds to the lower threshold of the confidence interval (advantageously for a probability of less than $P=0.05$ according to the Student's test) of the mean of the (Cl+P)/S ratios measured during large-scale studies on plants or plots suffering from S deficiency.

These large-scale studies make it possible to determine the reference (Cl+P)/S ratios for various plant species. It is then possible to constitute a database with the reference (Cl+P)/S ratios of various plant species. Such a database can then be used for carrying out the invention, in particular during step e).

In this particular embodiment, the chlorine (Cl) and phosphorus (P) content is measured in addition to the S and Mo content. Thus, the Mo/S and (Cl+P)/S ratios can be calculated and compared respectively to the reference Mo/S and (Cl+P)/S ratios as defined above. The applicants have shown, entirely surprisingly, that taking these two ratios (i.e. Mo/S and (Cl+P)/S) into account makes it possible to improve the accuracy and the reproducibility of the method of diagnosis according to the invention.

The applicants have noticed that there may be interference associated with the fact that the Mo content of the leaves can be increased under very specific conditions, for example when the soil is rich in Mo and/or when the soil is suffering from a deficiency of one or more of the mineral nutrients chosen from iron (Fe), copper (Cu), zinc (Zn), manganese (Mn) and boron (B). Under these specific conditions, it is possible to observe an increase in the Mo content of the leaves. The Mo/S ratio of a leaf sample may therefore be decreased without this necessarily resulting from a sulfur deficiency. On the other hand, and this is a major advantage of this embodiment, these specific conditions have no effect on the (Cl+P)/S ratio of a leaf sample.

Conversely, the applicants have noted that a soil rich in chlorine (Cl) or in phosphorus (P) is capable of decreasing the value of the (Cl+P)/S ratio of a leaf sample, but without affecting the Mo/S ratio of a leaf sample.

Thus, it is particularly advantageous to take into account the two ratios (i.e. Mo/S and (Cl+P)/S) during the implementation of the method of diagnosis according to the invention.

By taking into account the Mo/S and (Cl+P)/S ratios, it is therefore possible to determine 3 different sulfur nutrition states for a plant or a plot:
- Plant or plot not suffering from S deficiency: when the Mo/S and (Cl+P)/S ratios of the leaf sample are respectively less than the reference Mo/S and (Cl+P)/S ratios of a plant or of a plot not suffering from S deficiency;
- Plant or plot suffering from S deficiency: when the Mo/S and (Cl+P)/S ratios of the leaf sample are respectively greater than the reference Mo/S and (Cl+P)/S ratios of a plant or of a plot suffering from S deficiency;
- Plant or plot having a risk of S deficiency: when the Mo/S and (Cl+P)/S ratios of the leaf sample are respectively less than the reference Mo/S and (Cl+P)/S ratios of a plant or of a plot suffering from S deficiency and respectively greater than the reference Mo/S and (Cl+P)/S ratios of a plant or of a plot not suffering from S deficiency.

In one particular embodiment, the plant or the plot (i.e. the plant analyzed or the plot analyzed) is not suffering from sulfur deficiency and the Mo/S and (Cl+P)/S ratios of the leaf sample are respectively less than the reference Mo/S and (Cl+P)/S ratios of a plant or of a plot not suffering from S deficiency.

In another particular embodiment, the plant or the plot (i.e. the plant analyzed or the plot analyzed) is suffering from sulfur deficiency and the Mo/S and (Cl+P)/S ratios of the leaf sample are respectively greater than the reference Mo/S and (Cl+P)/S ratios of a plant or of a plot suffering from S deficiency.

In another particular embodiment, the plant or the plot (i.e. the plant analyzed or the plot analyzed) has a risk of sulfur deficiency and the Mo/S and (Cl+P)/S ratios of the leaf sample are respectively less than the reference Mo/S and (Cl+P)/S ratios of a plant or of a plot suffering from S deficiency and respectively greater than the reference Mo/S and (Cl+P)/S ratios of a plant or of a plot not suffering from S deficiency.

Preferred Plants

The method of diagnosis according to the invention is particularly suitable for plants or plots which require a significant provision of sulfur, that is to say plants or plots sensitive to sulfur deficiencies. In particular, the plant or the plot is chosen from rapeseed, in particular of the species *B. napus*, cabbage, in particular of the species *B. oleracea*, tomato, in particular of the species *S. lycopersicum*, corn, in particular of the species *Z. mays*, wheat, in particular of the species *T. aestivum*, pea, in particular of the species *P. sativum*, globe amaranth, *Arabidopsis thaliana* and barley, *Hordeum vulgare*.

Advantageously, the plant or the plot analyzed for its sulfur nutrition state is from the same species as the plant or the plot not suffering from sulfur deficiency (of step e)) and/or as the plant or the plot suffering from sulfur deficiency (of step e)).

The invention is also directed toward a method for diagnosing the sulfur nutrition state of a plant or of a plot, comprising the following steps:
a) taking a leaf sample from the plant or from the plot;
b) measuring the sulfur (S), chlorine (Cl) and phosphorus (P) content of the sample in mg/g;
c) calculating the (Cl+P)/S ratio;
e) comparing with a reference (Cl+P)/S ratio of a plant or of a plot not suffering from sulfur deficiency and/or of a plant or of a plot suffering from sulfur deficiency; and
f) deducing the sulfur nutrition state of the plant or of the plot.

It is then possible to determine, for each plant species, a reference ratio above which the plant is considered to be suffering from S deficiency (i.e. above the reference (Cl+P)/S ratio of a plant suffering from S deficiency), and a reference ratio below which the plant is considered to be not suffering from S deficiency (i.e. below the reference (Cl+P)/S ratio of a plant not suffering from S deficiency). It is therefore possible to determine 3 different sulfur nutrition states for a plant or a plot:

Plant or plot not suffering from S deficiency: when the (Cl+P)/S ratio of the sample taken is less than the reference (Cl+P)/S ratio of a plant or of a plot not suffering from S deficiency;

Plant or plot suffering from S deficiency: when the (Cl+P)/S ratio of the sample taken is greater than the reference (Cl+P)/S ratio of a plant or of a plot suffering from S deficiency;

Plant or plot having a risk of S deficiency: when the (Cl+P)/S ratio of the sample taken is less than the reference (Cl+P)/S ratio of a plant or of a plot suffering from S deficiency and greater than the reference (Cl+P)/S ratio of a plant or of a plot not suffering from S deficiency.

For example, for rapeseed (*B. napus*):
a plant or a plot is suffering from sulfur deficiency when the (Cl+P)/S ratio is greater than 3.21±0.5,
a plant or a plot is not suffering from S deficiency when the (Cl+P)/S ratio is less than 2.13±0.5,
a plant or a plot has a risk of sulfur deficiency when the (Cl+P)/S ratio is between 2.13±0.5 and 3.21±0.5.

As shown above, the method of diagnosis according to the invention is particularly advantageous for treating a sulfur deficiency or preventing a sulfur deficiency. It makes it possible in particular to identify the plants or the plots having a risk of sulfur deficiency in order to be able to treat them with a sulfur-containing fertilizer. Thus, the invention is also directed toward a method for adjusting the sulfur fertilization of a plant or of a plot, comprising the following successive steps:

A) carrying out the method of diagnosis according to the invention on the plant or the plot;
B) adding a sulfur-containing fertilizer if a sulfur deficiency or a risk of sulfur deficiency is detected during step A).

A sulfur deficiency is detected when:
the Mo/S ratio of the leaf sample is greater than the reference Mo/S ratio of a plant or of a plot suffering from sulfur deficiency; or
the Mo/S and (Cl+P)/S ratios of the leaf sample are respectively greater than the reference Mo/S and (Cl+P)/S ratios of a plant or of a plot suffering from sulfur deficiency.

A situation at risk of sulfur deficiency is detected when:
the Mo/S ratio of the leaf sample is (i) greater than the reference Mo/S ratio of a plant or of a plot not suffering from sulfur deficiency and (ii) less than the reference Mo/S ratio of a plant or of a plot suffering from sulfur deficiency; or
the Mo/S and (Cl+P)/S ratios of the leaf sample are respectively (i) greater than the reference Mo/S and (Cl+P)/S ratios of a plant or of a plot not suffering from sulfur deficiency and (ii) less than the reference Mo/S and (Cl+P)/S ratios of a plant or of a plot suffering from sulfur deficiency.

The sulfur fertilization of the plant or of the plot can then be adjusted in order to place the plant or the plot in a state not suffering from sulfur deficiency.

Several types of sulfur-containing fertilizers can be added in step B), for example sulfur-coated urea, ammonium sulfate, sulfur- and nitrogen-containing solutions, ammonium nitrate-sulfur, magnesium sulfate, potassium sulfate, superphosphate, sulfur-containing water-soluble fertilizers, sulfur-containing foliar fertilizers.

Thus, the method for adjusting the sulfur fertilization makes it possible to adjust the provisions of sulfur as a function of the needs of the plant. This method makes it possible in particular to prevent sulfur deficiencies which are capable of affecting the growth and/or the quality of the plant or of the plot.

The invention is also directed toward the use of the foliar Mo/S weight ratio, and optionally of the foliar (Cl+P)/S weight ratio, for determining the sulfur nutrition state of a plant or of a plot.

The invention is also directed toward the use of the foliar (Cl+P)/S weight ratio for determining the sulfur nutrition state of a plant or of a plot.

It being understood that the foliar Mo/S or (Cl+P)/S weight ratio corresponds to the Mo/S or (Cl+P)/S ratio as defined above.

The invention is illustrated in the examples below, which illustrate the invention without limiting the scope thereof.

FIGURE LEGENDS

FIG. 1: graph which represents the relative change (expressed as % relative to a plant not suffering from S deficiency) of the amount of several mineral nutrients (N, P, K, S, Ca, Mg, Fe, Cu, Zn, Mn, Mo, B and Na) in a *B. napus* plant suffering from S deficiency (i.e. without provision of sulfur). The plants were cultivated in a greenhouse and under hydroponic conditions. The amount of each element in a plant corresponds to the content of each element multiplied by the dry biomass of the whole plant.

Figure 2:
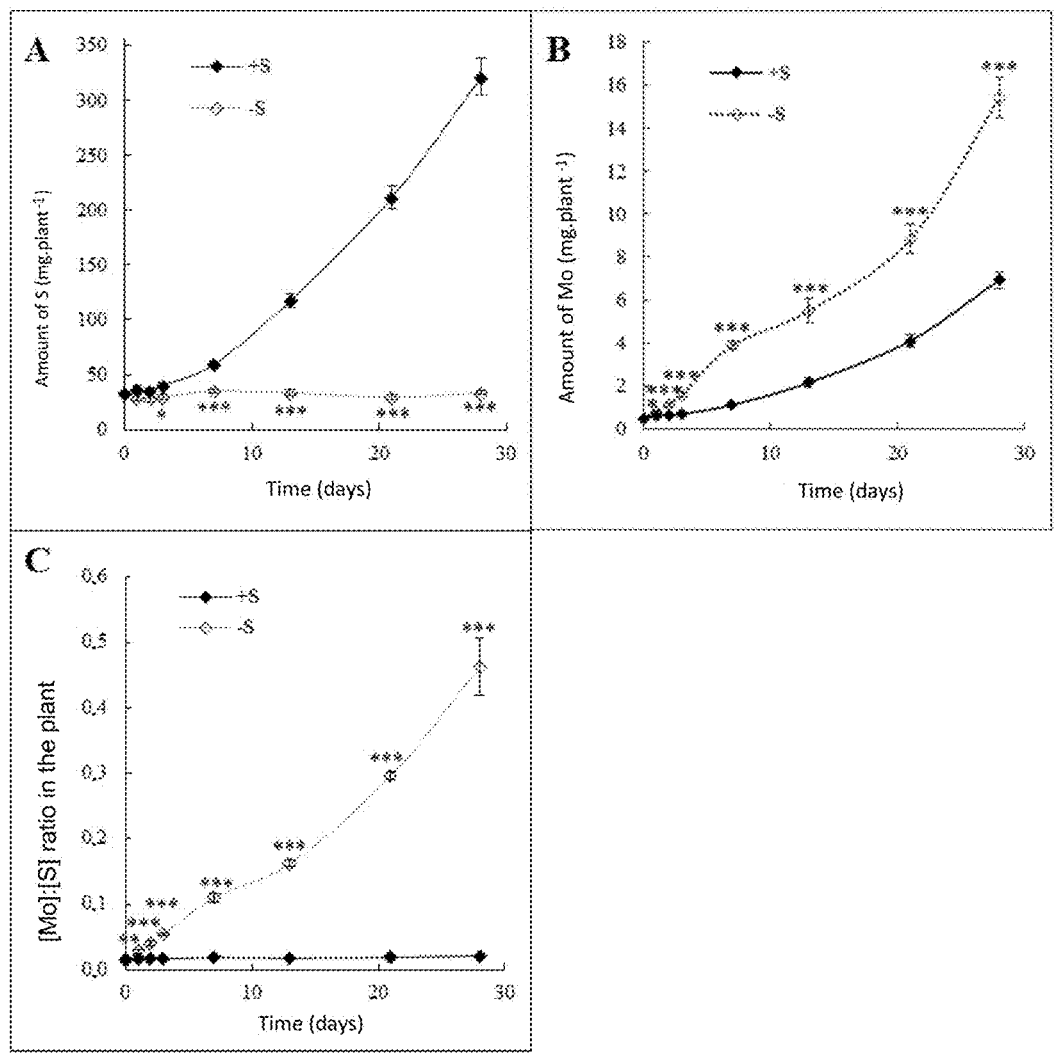

FIG. 2: graphs which represent: (A) the change in the amount of S in a *B. napus* plant suffering from S deficiency (−S) and in a *B. napus* plant not suffering from S deficiency (+S); (B) the change in the amount of Mo in a *B. napus* plant suffering from S deficiency (−S) and in a *B. napus* plant not suffering from S deficiency (+S); and (C) the change in the Mo/S ratio in a *B. napus* plant suffering from S deficiency (−S) and in a *B. napus* plant not suffering from S deficiency (+S). The plants were cultivated in a greenhouse and under hydroponic conditions. The amount of each element in a plant corresponds to the content of each element multiplied by the dry biomass of the whole plant.

Figure 3:
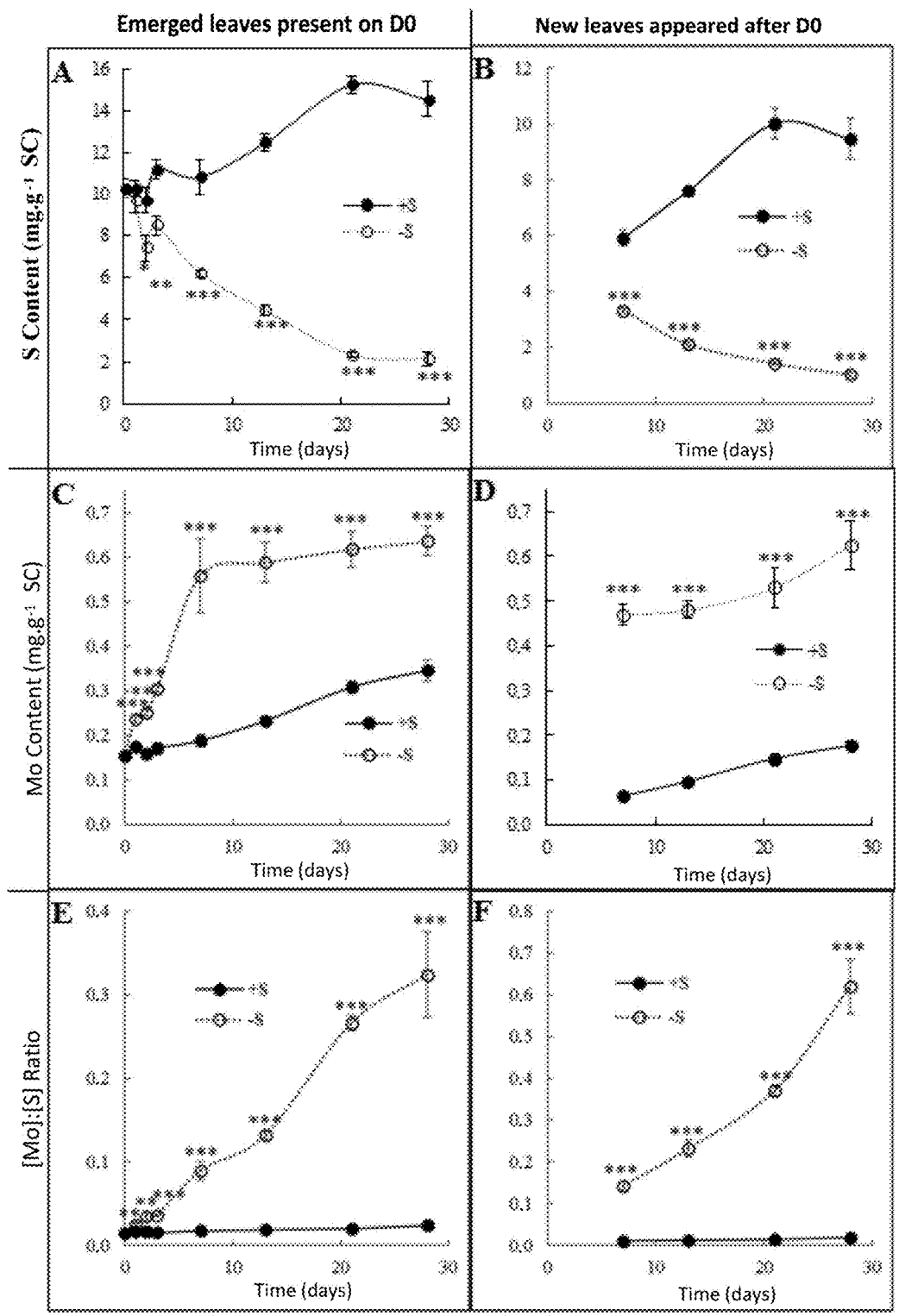

FIG. 3: graphs which represent the change in the S content (A and B), in the Mo content (C and D) and in the Mo/S ratio (E and F) in:
a sample of leaf emerged before the application of a sulfur deficiency (A, C and E), and
a sample of new leaf appearing during the sulfur deficiency (B, D and F)
of *B. napus* plants suffering from S deficiency (−S) and of *B. napus* plants not suffering from S deficiency (+S). The plants were cultivated in a greenhouse and under hydroponic conditions.

Figure 4:
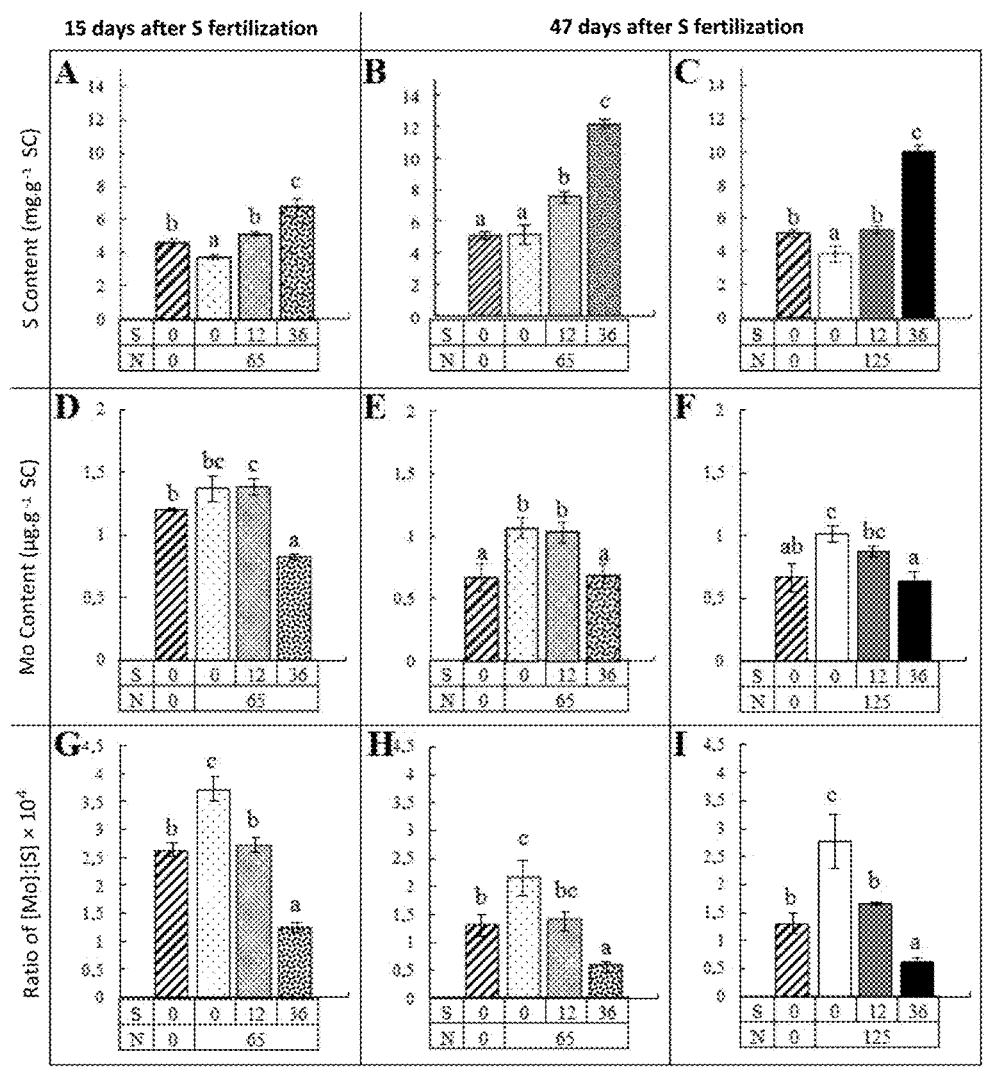

FIG. 4: graph which represents the S content (A, B and C), the Mo content (D, E, F) and the Mo/S ratio (G, H and I) of the leaves in samples of leaves from *B. napus* cultivated under open field conditions (i.e. +/−S fertilization and +/−N fertilization, expressed in kg/ha). The leaf samples were harvested 15 days (A, D, G) or 47 days (B, C, E, F, H, I) after a sulfur fertilization.

Figure 5:
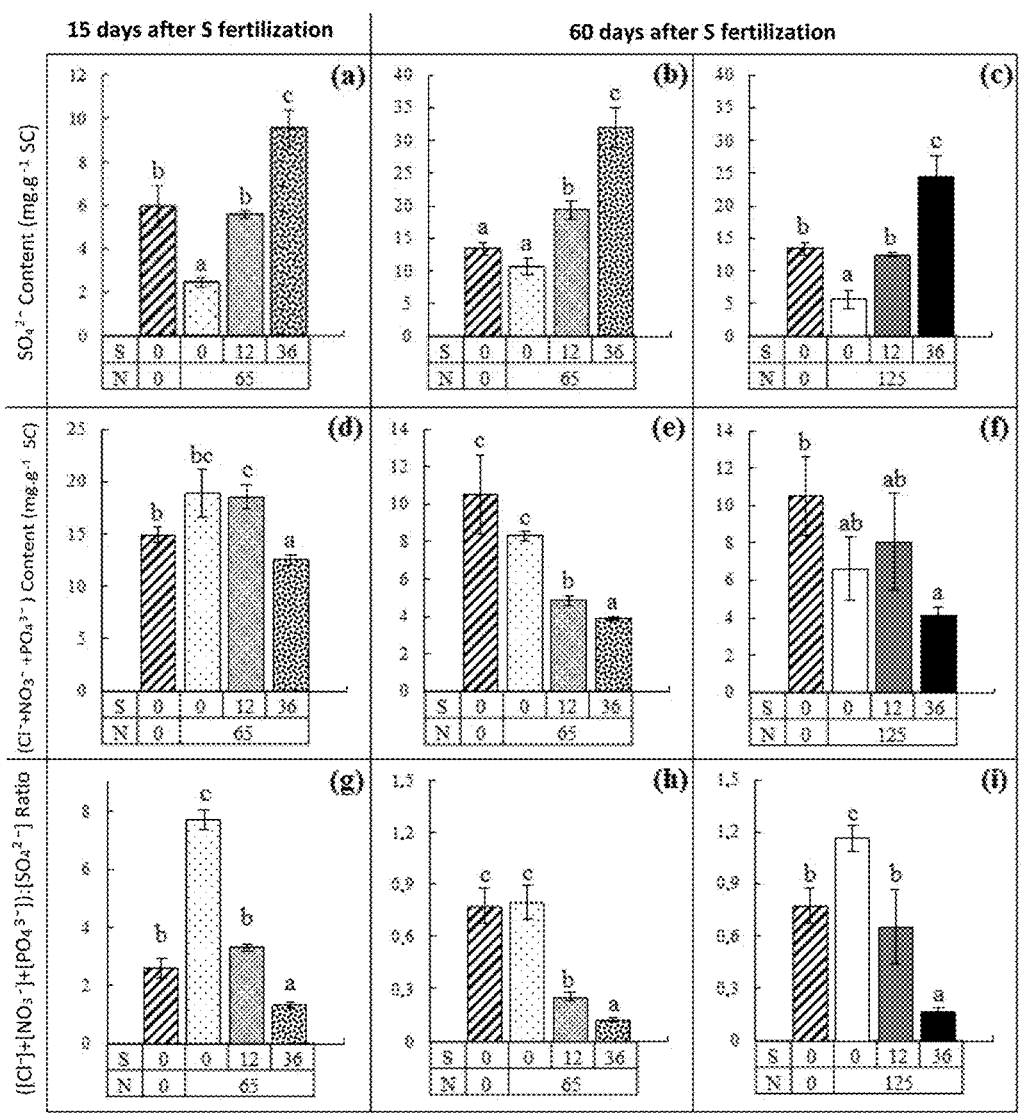

FIG. 5: graph which represents the $SO_4^{2-}$ content (A, B and C), the $(Cl^-+NO_3^-+PO_4^{3-})$ content (D, E and F) and the $(Cl^-+NO_3^-+PO_4^{3-})/SO_4^{2-}$ ratio (G, H and I) of leaf samples in samples of leaf from *B. napus* cultivated under open field conditions (i.e. +/−S fertilization and +/−N fertilization, expressed in kg/ha). The leaf samples were harvested 15 days (A, D, G) or 47 days (B, C, E, F, H, I) after a sulfur fertilization.

Figure 6:
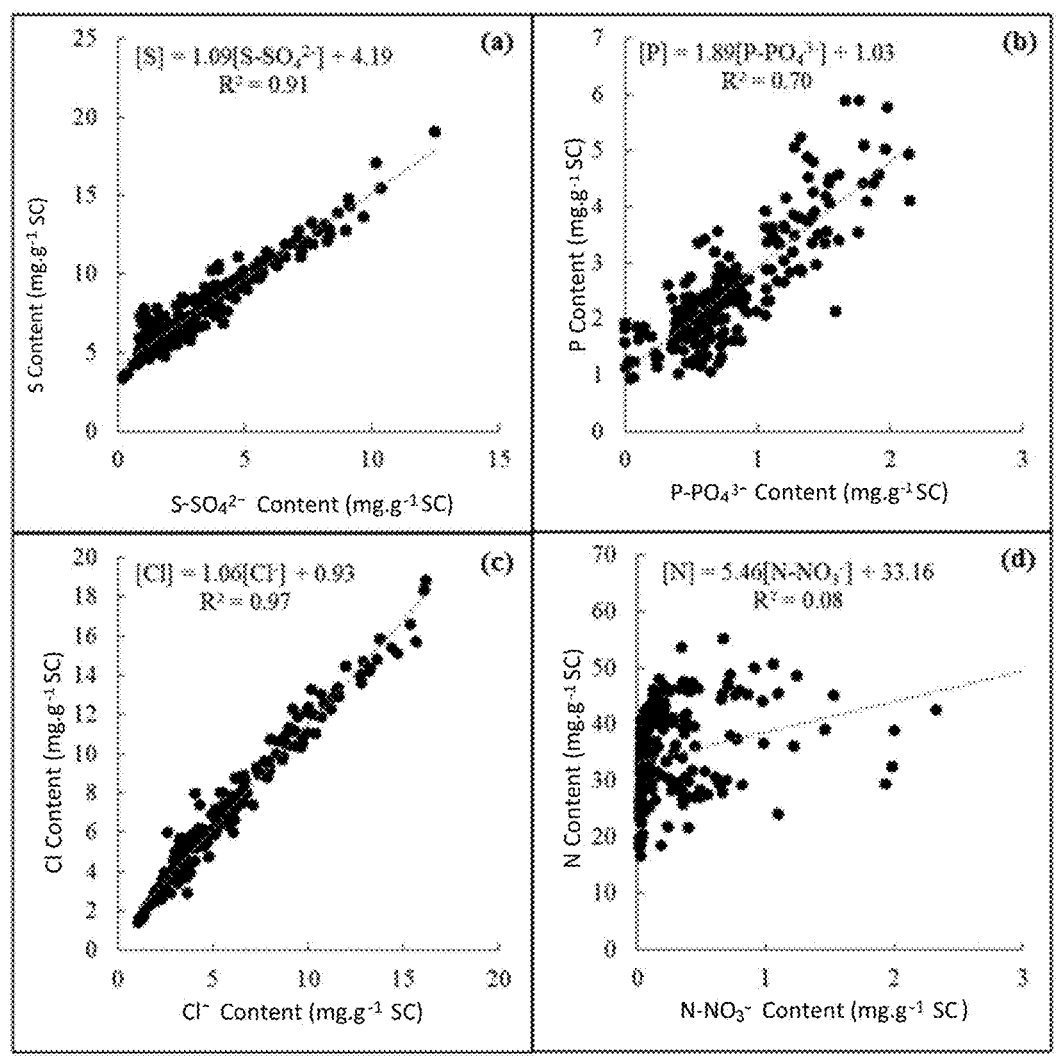

FIG. 6: graphs which show a correlation between the $SO_4^{2-}$, $PO_4^{3-}$, $Cl^-$ and $NO_3^-$ content and the S, P, Cl and N content respectively. The graphs show a correlation between the $SO_4^{2-}$, $PO_4^{3-}$, $Cl^-$ and S, P, Cl content respectively (A, B and C), but an absence of correlation between $NO_3^-$ and N (D).

Figure 7:
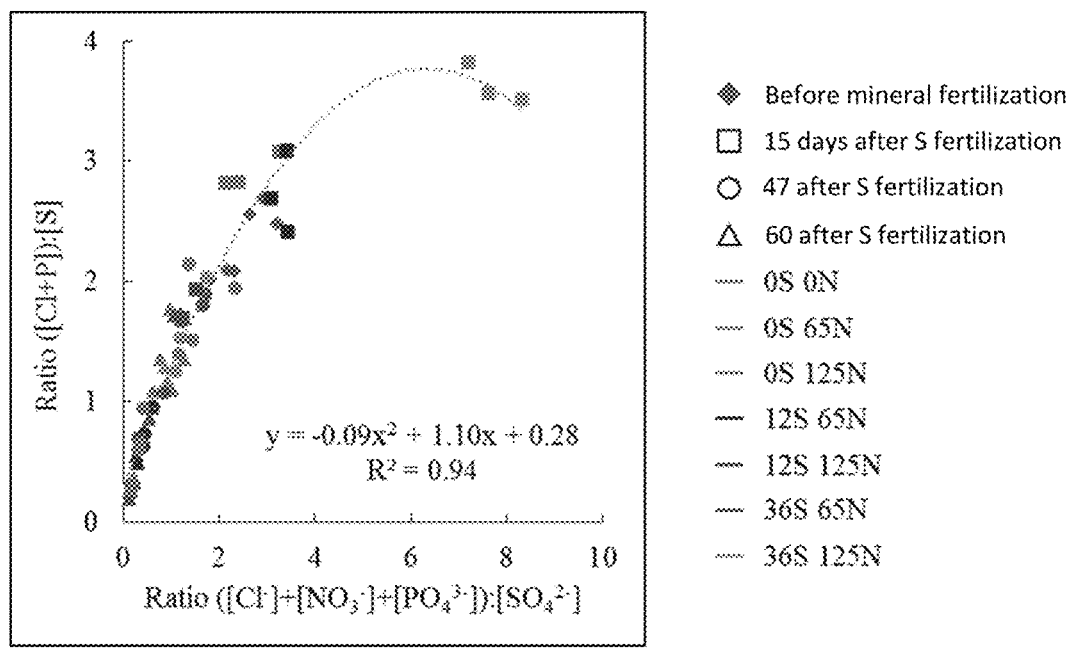

FIG. 7 graph which shows a correlation between the $(Cl^-+NO^{3-}+PO_4^{3-})/SO_4^{2-}$ ratio and the $(Cl+P)/S$ ratio.

EXAMPLES

Example 1

Preparation of the Leaf Samples for the Laboratory Tests on *B. napus*

Seeds of *B. napus* L. variety Boheme were germinated in demineralized water on perlite for 7 days in the dark and then 5 days in natural light. Just after the appearance of the first leaves, the sowings were placed in a greenhouse under hydroponic conditions, between October and December, at a temperature of 20° C. during the day and 15° C. at night.

The natural light was supplemented with sodium lamps (Master Greenpower T400W, Philips, Amsterdam, The Netherlands) (350 µmol·m$^{-2}$·s$^{-1}$ of photosynthetically active radiation) for 16 hours a day.

The nutritive solution for the sowings contained: 3.75 mM of $KNO_3$, 0.5 mM of $MgSO_4$, 0.5 mM of $CaCl_2$, 0.25 mM of $KH_2PO_4$, 0.2 mM of EDTA-2NaFe, 14 µM of $H_3BO_3$, 5 µM of $MnSO_4$, 3 µM of $ZnSO_4$, 0.7 µM of $CuSO_4$, 0.7 µM of $(NH_4)_6Mo_7O_{24}$, 0.1 µM of $CoCl_2$, 0.04 µM of $NiCl_2$ and buffered at pH 6.6 with 0.91 mM of $CaCO_3$. This solution was regularly renewed as a function of the disappearance of the $NO_3^-$ in the solution in order to maintain optimal nourishment conditions. For this purpose, the amount of $NO_3^-$ in the nutritive solution was measured using strips provided for this purpose (Merck Millipore, Darmstadt, Germany).

After 4 weeks of growth, the plants were separated into two batches fed with a nutritive solution suitable for optionally inducing a sulfur deficiency while at the same time maintaining one and the same concentration for the other elements of the nutritive solution:

Batch 1: Control plants (+S) cultivated with 508.7 µM of $SO_4^{2-}$,

Batch 2: Sulfur-deprived plants (−S) cultivated with 8.7 µM of $SO_4^{2-}$ (the presence of S is linked to the provision of $SO_4^{2-}$ of the trace elements of the nutritive solution, this amount is negligible).

These suitable nutritive solutions were also regularly renewed as a function of the disappearance of the $NO_3^-$ in the nutritive solution (approximately every two days at the end of the experiment).

The leaves present on day 0 (D0) were identified and labeled, and were considered to be "leaves emerged" before the application of the sulfur deficiency, while the leaves which appeared on the subsequent days were harvested separately and identified as "leaves appearing" after the application of the sulfur deficiency.

Four independent samples were taken on day 0 (D0), on day 1, 2, 3, 7, 13, 21 and on day 28 (D28). Day 0 corresponds to the day starting from which the plants were fed with a suitable nutritive solution. The four samples taken on each of the days each correspond to four control plants (+S) or four sulfur-deprived plants (−S).

The whole plants were then frozen in liquid nitrogen and stored at −80° C. for subsequent analysis. For each of the samples, a subsample of leaf was freeze-dried and ground to fine powder using a ball mill (MM400, Retsch, Haan, Germany). The powder thus obtained was used for measuring the content of the various mineral nutrients.

Example 2

Measurement of the Mineral Nutrient Content by Mass Spectrometry a) Measurement of the Sulfur (S) and Nitrogen (N) Content In order to measure the sulfur (S) and nitrogen (N) content, 4 mg of solids (SC) of powder were placed in tin capsules. The amount of S or N was determined with a continuous flow isotope ratio mass spectrometer (Nu Instruments, Wrexham, United Kingdom) coupled to a C/N/S analyzer (EA3000, Euro Vector, Milan, Italy). The total S content ($S_{tot}$) or the total N content ($N_{tot}$) at a time "t" was measured as follows:

$$S_{tot}(\text{or } N_{tot}) = [\% \ S_t(\text{or } N_t) \times SC_t] \times 100$$

b) Measurement of the Content of the Other Mineral Nutrients

The measurement of the P, K, Ca, Mg, Fe, Cu, Zn, Mo, Mn, B, Ni and Na content in the leaf samples was carried out with a high-resolution plasma mass spectrometer (HR ICP-MS, Thermo Scientific, Element 2™, Bremen, Germany) after digestion of the powder prepared according to example 1 by an add and microwave treatment (Multiwave ECO, Anton Paar, Ies Ulis, France) using 800 µl of $HNO_3$ (Thermo Fischer, Illkirch, France), 200 µl of $H_2O_2$ (SCP Science, Quebec, Canada) and 1 ml of Milli-Q water for 40 mg of solids (SC). Each leaf sample was supplemented with two internal standards, gallium and rhodium (SCP Science, Quebec, Canada), at a final concentration of 10 and 2 µg·l$^{-1}$, respectively, and diluted with Milli-Q water in order to obtain a solution containing 2.0% (v/v) of nitric acid. This solution was then filtered on a 40 µm Teflon filtration system (Courtage Analyses Services, Mont-Saint-Aignan, France). The mineral nutrient content was measured using standard curves prepared and verified with a certified reference of lemon tree leaves (CRM NCS ZC73018, Sylab, Metz, France). The mineral nutrient content was then calculated using the same formula as for S and N.

Example 3

Impact of a Sulfur Deficiency on the Mineral Nutrient Content

The content of several mineral nutrients was measured for samples prepared according to example 1, after 21 days of sulfur deficiency (D21). The data are presented in the form of mean±standard deviation for the four samples of 4 plants. All the data were analyzed using the Student's test (Excel software) and marked with one or more asterisks when the difference is significant between the (+S) and (−S) samples (*P<0.05, P<0.01, *P<0.001). The results are presented in FIG. 1.

As expected, after 21 days of S deficiency, the absorption of S is decreased by −100.7±0.90% compared with the (+S) plants. The absorption of other mineral nutrients was also decreased: N (−8.7±1.06%), K (−20.2±0.88%), Ca (−22.0±2.41%) and Na (−23.4±1.85%). The adsorption of B is, for its part, more greatly decreased (−52.9±2.82%). Conversely, the S deficiency greatly increases the absorption of Mo (+197.0±10.73%). The absorption of P, Mg, Fe, Cu, Zn and Mn is not affected by the S deficiency.

Example 4

Change in the Mo/S Ratio During an S Deficiency

The S and Mo content of various tissues of the plants (leaves, roots) was measured for samples prepared according to example 1, on day 0 (D0), on day 1 (D1), 2, 3, 7, 13, 21 and on day 28 (D28). FIG. 2 presents the S or Mo content and the Mo/S ratio in the form of mean±standard deviation in four plants. All the data were analyzed using the Student's test (Excel software) and marked with one or more asterisks when the difference is significant between the (+S) and (−S) samples (*P<0.05, P<0.01, *P<0.001). The results are presented in FIG. 2.

The amount of S of the sulfur-deprived (−S) plants remained at a basal level (FIG. 2A) indicating an absence of absorption of S. The amount of S of the control (+S) plants constantly increases over time and is significantly higher than for the sulfur-deprived (−S) plants starting from D3.

Conversely, the amount of Mo of the sulfur-deprived (−S) plants and of the control (+S) plants increases over time, but to a higher level for the sulfur-deprived (−S) plants (FIG. 2B). For example, the amount of Mo is 2.23 times greater for the sulfur-deprived (−S) plants compared with the control (+S) plants on D28. As early as the first day, the amount of Mo of the sulfur-deprived (−S) plants is 28% greater than for the control (+S) plants. This difference becomes much more marked starting from D3.

Consequently, the Mo/S ratio in the sulfur-deprived (−S) plants increases significantly starting from D1, and is approximately 21 times greater on D28 (FIG. 2C). The Mo/S ratio of the control (+S) plants does not increase over time.

Conclusion: The Mo/S ratio makes it possible to significantly distinguish a plant suffering from sulfur deficiency and a plant not suffering from sulfur deficiency.

Example 5

Change in the Mo/S Ratio During an S Deficiency for Various Types of Leaf

The S and Mo content was measured for samples prepared according to example 1 on day 0 (D0), on day 1, 2, 3, 7, 13, 21 and on day 28 (D28), by distinguishing the "leaves emerged" before the sulfur deficiency and the "new leaves" appearing during the sulfur deficiency.

It was shown that, regardless of the type of leaf analyzed, the S deficiency decreases the S contents but increases the Mo contents (FIGS. 3A-F). Consequently, the Mo/S ratio increases over time in the leaves of the plants suffering from sulfur deficiency (FIGS. 3E-F), this being regardless of the type of leaf analyzed.

Conclusion: The Mo/S ratio of the leaves is increased very early on during a sulfur deficiency, regardless of the type of leaf.

Example 6

Change in the Mo/S Ratio after an S Fertilization and Impact of N Fertilization

A field of rapeseed (*B. napus*), was divided into three distinct plots, each having a different S fertilization level, of 36, 12 or 0 kg S ha$^{-1}$.

Each of the plots was subdivided into three, each subdivision having a different N fertilization level (0, 65 or 125 kg N ha$^{-1}$).

Leaf samples were taken in each of the subdivisions. The S and Mo content was measured for each sample at 15 and 47 days after S fertilization.

The S content was significantly reduced under the S deficiency condition, independently of the N fertilization level (65 or 125 kg N ha$^{-1}$) (FIG. 4A-C). The highest Mo content was observed in the plants having received N fertilization without or with little S fertilization (0 or 12 kg S ha$^{-1}$) (FIG. 4D-F). The Mo/S ratio made it possible to differentiate the plots as a function of their S fertilization level 0, 12 and 36 kg S ha$^{-1}$ (FIG. 4G-I). Indeed, the plants with N fertilization (65 or 125 kg N ha$^{-1}$) and without S fertilization had the highest Mo/S ratio, whereas the plants with S fertilization at 36 kg S ha$^{-1}$ had the lowest Mo/S ratio. The plants with S fertilization at 12 kg S ha$^{-1}$ had an intermediate Mo/S ratio.

Interactions were observed between the N fertilization and the S fertilization. It may be assumed that the level of growth of the plants was significantly reduced in the absence of N fertilization. For example, 15 days after the S fertilization, the biomass of the mature leaves was 5.03±0.38 g SC leaf$^{-1}$ in the non-N-fertilized plot, whereas the biomass in the N-fertilized plot with 65 kg N ha$^{-1}$ was 6.70±0.01 g SC leaf$^{-1}$ (p<0.01). This decrease in the growth of the non-N-fertilized plants had a direct impact on the S content given that the S requirements of the non-N-fertilized plants were not as great as for the N-fertilized plants. Indeed, the N-fertilized plants consumed more S to ensure their growth. Thus, the Mo/S ratio was significantly lower (FIG. 4G-I) in the absence of N fertilization, which reflects a lower S requirement for the non-N-fertilized plants.

Likewise, it was observed that the Mo/S ratio was higher for the plants with the highest N fertilization level (i.e. 125 kg N ha$^{-1}$) independently of the S fertilization level, which also reflects the higher S requirement of the N-fertilized plants.

Conclusion: This example therefore shows that the Mo/S ratio of the leaves can also be used for plants cultivated under open field conditions. The Mo/S ratio can give early and long-lasting discrimination of the plants having variable S availabilities (provided in this example by an S fertilization).

Example 7

Reproducibility on Various Plant Species

The Mo/S ratio was calculated on samples of leaf from various plant species: *B. oleracea, T. aestivum, Z. mays, P. sativum* and *S. lycopersicum*, under growth conditions in a greenhouse and during which the provision of sulfur was eliminated or reduced.

For each of the species, under conditions of S deficiency, the S content was significantly reduced and the Mo content was significantly increased (Table 1, below).

| Species | Number of days of treatment | S (mg · g$^{-1}$ SC) +S | S (mg · g$^{-1}$ SC) −S | Mo (ug · g$^{-1}$ SC) +S | Mo (ug · g$^{-1}$ SC) −S | [Mo]:[S] Ratio +S | [Mo]:[S] Ratio −S |
|---|---|---|---|---|---|---|---|
| B. napus | 0 | 10.33 ± 0.46 | | 154.57 ± 10.16 | | 149.75 ± 7.34 | |
| | 1 | 10.30 ± 0.39 | 9.70 ± 0.56 | 175.35 ± 6.87 | 237.01 ± 7.700*** | 170.23 ± 1.12 | 247.40 ± 18.67** |
| | 21 | 15.25 ± 0.39 | 2.33 ± 0.14*** | 308.49 ± 14.02 | 617.82 ± 40.08*** | 202.21 ± 6.52 | 2660.38 ± 91.28*** |
| B. oleracea | 20 | 4.83 ± 0.46 | 1.90 ± 0.04*** | 4.02 ± 0.21 | 5.03 ± 0.16** | 8.44 ± 0.49 | 26.53 ± 1.16*** |
| T. aestivum | 2 | 3.60 ± 0.18 | 3.45 ± 0.22 | 90.17 ± 9.43 | 201.48 ± 7.72*** | 249.52 ± 18.17 | 584.45 ± 24.95*** |
| | 8 | 3.47 ± 0.06 | 3.12 ± 0.00** | 85.14 ± 1.23 | 719.90 ± 36.62*** | 245.32 ± 5.56 | 2306.22 ± 110.52*** |
| | 24 | 3.37 ± 0.02 | 1.85 ± 0.05*** | 79.83 ± 2.08 | 977.11 ± 32.63*** | 236.67 ± 5.58 | 5285.33 ± 236.13*** |
| Z. mays | 0 | 2.82 ± 0.10 | | 22.62 ± 0.85 | | 80.18 ± 1.54 | |
| | 5 | 3.05 ± 0.03 | 2.11 ± 0.13*** | 24.67 ± 0.48 | 468.16 ± 28.15*** | 80.86 ± 0.82 | 2224.10 ± 72.16*** |
| | 18 | 2.39 ± 0.05 | 0.95 ± 0.04*** | 27.95 ± 1.65 | 562.63 ± 34.46*** | 116.67 ± 5.06 | 5934.41 ± 137.28*** |
| P. sativum | 0 | 2.75 ± 0.09 | | 20.48 ± 4.22 | | 73.76 ± 12.95 | |
| | 19 | 2.73 ± 0.10 | 2.20 ± 0.14* | 9.43 ± 0.50 | 12.46 ± 0.34** | 34.49 ± 0.67 | 57.63 ± 5.58** |
| S. lycopersicum | 65 | 10.10 ± 0.71 | 1.83 ± 0.27*** | 2.86 ± 0.03 | 5.09 ± 0.82* | 2.88 ± 0.21 | 27.90 ± 1.96*** |

The results show that the Mo/S ratio was significantly increased under the S deficiency condition. The value of the Mo/S ratio was specific for the plant species analyzed, with values ranging from 3 to 250 for the reference Mo/S ratio (i.e. control or +S plant) and from 27 to 5934 for the plants suffering from S deficiency (i.e. −S).

Conclusion: Mo/S ratio is a reliable indicator for diagnosing the sulfur nutrition state independently of the plants species under consideration.

Example 8

Impact of the Sulfur Deficiency on the Cl and P Content and Advantage of the (Cl+P)/S Ratio a) Analysis of the $SO_4^{2-}$, $PO_4^{3-}$, $Cl^-$ and $NO_3^-$ Ions The ions were extracted from 30 mg of a ground and freeze-dried sample of leaf of *B. napus* cultivated in an open field with various N and S fertilization levels according to the modes of example 6.

The ions were extracted from the sample according to the steps below:
(i) in a first step, the leaf sample was placed in 1.5 ml of a concentrated ethanol solution at 50%,
(ii) the solution obtained was then incubated at 40° C. for 1 hour,
(iii) the solution was then centrifuged at 12000 g for 20 min,
(iv) the supernatant was collected,
(v) the pellet was resuspended in 1.5 ml of water and then incubated for one hour at 95° C.,
(vi) the centrifugation (iii) and collection (iv) steps were repeated a second time and the two supernatants obtained in step (iv) were mixed.

The supernatants were then evaporated under vacuum (Concentrator Evaporator RC 10.22, Jouan, Saint-Herblain, France). The dry residue was redissolved in 1.5 ml of ultra pure water and was filtered through a 45 μm filter.

The anion content was then measured by HPLC with a conductivity detector (ICS3000, Thermo Scientific-Dionex, Villebon-sur-Yvette, France) using a running buffer containing 4.05 mM $Na_2CO_3$ and 1.26 mM $NaHCO_3$ and through an analytical column (AS22 4*250 mm, Thermo Scientific-Dionex, Villebon-sur-Yvette, France).

b) Analysis of the Mineral Nutrients S, P, Cl and N

After drying and grinding, leaf samples were placed in a dish and the S, P and Cl content was determined by X-ray fluorescence spectrometry (Portable XRF S1 Titan 800, Bruker, Kalkar, Germany).

The S, P and Cl content was determined using calibration curves obtained by a high-resolution plasma mass spectrometer (HR ICP-MS, Thermo Scientific, Element 2™, Bremen, Germany).

Example 9

Interest and Rationale of Taking into Account the (Cl+P)/S Ratio a) Interest of the $(Cl^-+NO_3^-+PO_4^{3-})/SO_4^{2-}$ Ratio A field of rapeseed was divided into three distinct plots, each having been fertilized with S on D0 (i.e. first day of S fertilization) with various amounts of S, of 36, 12 or 0 kg S ha$^{-1}$.

The three plots were subdivided into three, each subdivision having a different N fertilization level, 0, 65 or 125 kg N ha$^{-1}$.

Leaf samples were taken in each of the subdivisions (i.e. in the 6 subdivisions). The $SO_4^{2-}$, $Cl^-$, $NO_3^-$ and $PO_4^{3-}$ content and the $(Cl^-+NO_3^-+PO_4^{3-})/SO_4^{2-}$ ratio were measured in the samples at 15 (D15) and 60 (D60) days after the S fertilization (or non-S-fertilization for the two subdivisions having an S fertilization level of 0 kg S ha$^{-1}$).

The $SO_4^{2-}$ content in the leaf samples was significantly reduced under the low S fertilization condition (FIG. 5a-c), independently of the N fertilization level. The decrease in the $SO_4^{2-}$ content was compensated for by an increase in the $Cl^-$, $NO_3^-$ and $PO_4^{3-}$ content (FIG. 5d-f). The lowest $(Cl^-+NO_3^-+PO_4^{3-})$ content was measured in the leaf samples from the plants fertilized with the highest dose of S (i.e. 36 kg S ha$^{-1}$). The leaf samples from the plants fertilized with N (65 or 125 kg N ha$^{-1}$), without S fertilization, had the highest $(Cl^-+NO_3^-+PO_4^{3-})/SO_4^{2-}$ ratio. The leaf samples from the plants fertilized with 36 kg S ha$^{-1}$ of S had the lowest $(Cl^-+NO_3^-+PO_4^{3-})/SO_4^{2-}$ ratio. The leaf samples from the plants fertilized with 12 kg S ha$^{-1}$ of S had an intermediate $(Cl^-+NO_3^-+PO_4^{3-})/SO_4^{2-}$ ratio. The $(Cl^-+NO_3^-+PO_4^{3-})/SO_4^{2-}$ ratio therefore made it possible to differentiate the three plots as a function of their S fertilization level (36, 12 or 0 kg S ha$^{-1}$) (FIG. 5G-I).

Interactions were observed between the N fertilization and the S fertilization. It may be assumed that the level of growth of the plants was significantly reduced in the absence of N. For example, on D15, the biomass of the leaves was 5.03±0.38 g SC leaf$^{-1}$ for the non-N-fertilized plants, whereas the biomass of the plants fertilized with 65 kg N ha$^{-1}$ was 6.70±0.01 g SC leaf$^{-1}$ (p<0.01). This decrease in the growth of the non-N-fertilized plants had a direct impact on the $SO_4^{2-}$ content given that the $SO_4^{2-}$ requirements of the non-N-fertilized plants were lower than for the N-fertilized plants. Indeed, the plants fertilized with N used more $SO_4^{2-}$ to ensure their growth. For example, for one and the same S fertilization level, the $SO_4^{2-}$ content in the leaf samples from the plants without N fertilization was significantly higher than (FIGS. 5A and C) or similar to (FIG. 5B) the content in the leaf samples from the plants receiving an N fertilization.

However, the $(Cl^-+NO_3^-+PO_4^{3-})$ content in the leaf samples from the plants with N fertilization and without S fertilization was unchanged compared with the $(Cl^-+NO_3^-+PO_4^{3-})$ content of the leaf samples from the plants without N fertilization (FIG. 5d-f). Consequently, the $(Cl^-+NO_3^-+PO_4^{3-})/SO_4^{2-}$ ratio was significantly decreased (FIGS. 5g and i) or was similar (FIG. 5h) in the absence of N fertilization, which reflects a lower S requirement.

Similarly, the growth of the plants was further stimulated with an N fertilization of 125 kg N ha$^{-1}$, which had the effect of increasing the S requirements and of reducing the $SO_4^{2-}$ content in the leaves (p<0.05). This observation is illustrated in FIGS. 5b and c.

It was also observed, by comparing FIGS. 6h and 6i, that the $(Cl^-+NO_3^-+PO_4^{3-})/SO_4^{2-}$ ratio was increased for the plants having received the highest dose of N (i.e. 125 kg N ha$^{-1}$), which reflects a higher S requirement for these plants.

The $(Cl^-+NO_3^-+PO_4^{3-})/SO_4^{2-}$ ratio was also calculated on leaf samples from other species cultivated in an open field (*B. oleracea, T. aestivum, Z. mays, M. truncatula, S. lycopersicum* and *B. napus*) under controlled fertilization conditions, with S fertilization (+S) or sulfur deficiency (–S). The results are presented in Table 2 below.

Firstly, it was shown, on the rapeseed leaf samples, that the content of $Cl^-$, $NO_3^-$, $PO_4^{3-}$ and $SO_4^{2-}$ ions correlated with the Cl, N, P and S content, respectively.

FIG. 6 shows a correlation between the content of $Cl^-$, $NO_3^-$, $PO_4^{3-}$ and $SO_4^{2-}$ ions (measured by HPLC) and the Cl, N, P and S content (measured by X-ray fluorescence spectrometry). The $Cl^-$, $PO_4^{3-}$ and $SO_4^{2-}$ content correlates strongly with the Cl, P and S content (FIG. 6a-c) with correlation coefficients of 0.97, 0.70 and 0.91, respectively.

Conversely, no correlation between the $NO_3^-$ content and the N content was observed (FIG. 6d).

Subsequently, it was shown that the $(Cl^-+NO_3^-+PO_4^{3-})/SO_4^{2-}$ ratio correlated significantly with the (Cl+P)/S ratio (FIG. 7), with a correlation coefficient of 0.94. FIGS. 8b and 8c show that this correlation is independent of the developmental stage of the plant.

Conclusion: The (Cl+P)/S ratio is a reliable indicator which is easy to implement for diagnosing the sulfur nutrition state of a plant.

The invention claimed is:

1. A method for diagnosing the sulfur nutrition state of a plant or plot, comprising the following steps:
   a) taking a leaf sample from the plant or taking a leaf sample representative of the plot;
   b) measuring the sulfur (S), chlorine (Cl) and phosphorus (P) content of the sample in mg/g;
   c) measuring the molybdenum (Mo) content of the sample in μg/g;
   d) calculating the Mo/S ratio and the (Cl+P)/S ratio;
   e) comparing with a reference Mo/S ratio and a reference (Cl+P)/S ratio of a plant or plot not suffering from

| Species | Number of days of treatment | $SO_4^{2-}$ (mg · g$^{-1}$ SC) +S | $SO_4^{2-}$ (mg · g$^{-1}$ SC) –S | $(Cl^- + NO_3^- + PO_4^{3-})$ content (mg · g$^{-1}$ SC) +S | $(Cl^- + NO_3^- + PO_4^{3-})$ content (mg · g$^{-1}$ SC) –S | $[(Cl^-] + [NO_3^-] + [PO_4^{3-}]):[SO_4^{2-}]$ Ratio +S | $[(Cl^-] + [NO_3^-] + [PO_4^{3-}]):[SO_4^{2-}]$ Ratio –S |
|---|---|---|---|---|---|---|---|
| *B. napus* | 0 | 8.13 ± 0.61 | | 56.79 ± 7.37 | | 2.34 ± 0.28 | |
| | 3 | 8.73 ± 0.41 | 5.30 ± 0.48*** | 63.65 ± 0.96 | 70.86 ± 5.68 | 2.44 ± 0.11 | 4.53 ± 0.39** |
| | 13 | 9.95 ± 0.17 | 2.68 ± 0.16*** | 62.83 ± 5.86 | 86.42 ± 4.66** | 2.11 ± 0.20 | 10.74 ± 0.17*** |
| *B. oleracea* | 135 | 7.05 ± 1.22 | 0.35 ± 0.04*** | 44.9 ± 6.85 | 61.87 ± 3.27* | 6.60 ± 1.06 | 192.24 ± 40.89** |
| *T. aestivum* | 0 | 3.03 ± 0.09 | | 63.58 ± 0.80 | | 21.02 ± 0.76 | |
| | 8 | 0.94 ± 0.05 | 1.15 ± 0.03** | 59.34 ± 2.10 | 68.04 ± 0.84** | 30.54 ± 0.53 | 59.60 ± 2.36*** |
| | 16 | 2.17 ± 0.06 | 0.50 ± 0.05*** | 64.79 ± 1.29 | 70.19 ± 1.80* | 30.01 ± 1.28 | 146.03 ± 15.81*** |
| *Z. mays* | 0 | 2.02 ± 0.49 | | 74.74 ± 1.55 | | 42.15 ± 7.16 | |
| | 5 | 3.44 ± 0.07 | 1.39 ± 0.08** | 78.31 ± 2.82 | 91.71 ± 1.28** | 22.83 ± 1.09 | 66.49 ± 3.45*** |
| | 18 | 1.38 ± 0.05 | 0.27 ± 0.02*** | 70.38 ± 3.46 | 103.28 ± 0.79*** | 51.01 ± 2.19 | 384.67 ± 23.44*** |
| *S. lycopersicum* | 75 | 63.75 ± 4.79 | 50.39 ± 2.42* | 68.84 ± 4.61 | 84.77 ± 2.44* | 1.11 ± 0.15 | 1.69 ± 010** |
| *M. truncatula* | 0 | 3.31 ± 0.16 | | 25.32 ± 0.60 | | 7.68 ± 0.21 | |
| | 8 | 3.60 ± 0.12 | 0.15 ± 0.03*** | 25.40 ± 1.54 | 34.27 ± 3.44* | 7.07 ± 0.48 | 231.78 ± 25.21*** |
| | 21 | 4.75 ± 0.18 | 0.26 ± 0.01*** | 25.92 ± 1.94 | 34.90 ± 2.46* | 5.49 ± 0.50 | 133.04 ± 12.48*** |

The results show that the $(Cl^-+NO_3^-+PO_4^{3-})/SO_4^{2-}$ ratio was significantly increased under the S deficiency condition regardless of the species. The values for the $(Cl^-+NO^{3-}+PO_4^{3-})/SO_4^{2-}$ ratio are specific for the plant species analyzed.

Conclusion: The decrease in the $SO_4^{2-}$ content is compensated by an increase in the $(Cl^-+NO_3^-+PO_4^{3-})$ content, and therefore an increase in the $(Cl^-+NO_3^-+PO_4^{3-})/SO_4^{2-}$ ratio. Consequently, the $(Cl^-+NO_3^-+PO_4^{3-})/SO_4^{2-}$ ratio is an indicator which makes it possible to diagnose the sulfur nutrition state of a plant, independently of the plant species under consideration.

b) Validation of the (Cl+P)/S Ratio

In order to facilitate the implementation of the invention, a simplification of the calculation of the $(Cl^-+NO_3^-+PO_4^{3-})/SO_4^{2-}$ ratio was sought.

sulfur deficiency, and/or with a reference Mo/S ratio and a reference (Cl+P)/S ratio of a plant or plot suffering from sulfur deficiency; and
   f) deducing the sulfur nutrition state of the plant or plot.

2. The method as claimed in claim 1, wherein the plant has been cultivated in an open field.

3. The method as claimed in claim 2, wherein:
   the plant or the plot is suffering from sulfur deficiency and the Mo/S ratio of the leaf sample is greater than the reference Mo/S ratio of a plant or of a plot suffering from sulfur deficiency;
   the plant or the plot is not suffering from sulfur deficiency and the Mo/S ratio of the leaf sample is less than the reference Mo/S ratio of a plant or of a plot not suffering from sulfur deficiency; or
   the plant or the plot has a risk of sulfur deficiency and the Mo/S ratio of the leaf sample is less than the reference Mo/S ratio of a plant or of a plot suffering from sulfur deficiency, and the Mo/S ratio of the leaf sample is greater than the reference Mo/S ratio of a plant or of a plot not suffering from sulfur deficiency.

4. The method as claimed in claim 2, wherein:
the plant or the plot is suffering from sulfur deficiency and the Mo/S and (Cl+P)/S ratios of the leaf sample are respectively greater than the reference Mo/S and (Cl+P)/S ratios of a plant or of a plot suffering from sulfur deficiency,
the plant or the plot is not suffering from sulfur deficiency and the Mo/S and (Cl+P)/S ratios of the leaf sample are respectively less than the reference Mo/S and (Cl+P)/S ratios of a plant or of a plot not suffering from sulfur deficiency, or
the plant or the plot has a risk of S deficiency and the Mo/S and (Cl+P)/S ratios of the leaf sample are respectively less than the reference Mo/S and (Cl+P)/S ratios of a plant or of a plot suffering from S deficiency and respectively greater than the reference Mo/S and (Cl+P)/S ratios of a plant or of a plot not suffering from S deficiency.

5. The method as claimed in claim 2, wherein the plant or the plot is chosen from rapeseed, cabbage, tomato, corn, wheat, pea, globe amaranth, and barley.

6. The method as claimed in claim 2, wherein the plant or the plot analyzed for its sulfur nutrition state is from the same species as the plant or the plot not suffering from sulfur deficiency and/or as the plant or the plot suffering from sulfur deficiency.

7. The method as claimed in claim 2, wherein the leaf sample is dried and ground before steps b) and c).

8. The method as claimed in claim 2, wherein steps b) and c) are carried out by X-ray fluorescence spectrometry or by plasma mass spectrometry.

9. The method as claimed in claim 2, wherein steps b) and c) are carried out simultaneously.

10. The method as claimed in claim 2, wherein the plant or the plot is a plant of the species *B. napus, B. oleracea, S. lycopersicum, Z. mays, T. aestivum, P. sativum, Arabidopsis thaliana*, or *Hordeum vulgare*.

11. The method as claimed in claim 1, wherein:
the plant or the plot is suffering from sulfur deficiency and the Mo/S ratio of the leaf sample is greater than the reference Mo/S ratio of a plant or of a plot suffering from sulfur deficiency;
the plant or the plot is not suffering from sulfur deficiency and the Mo/S ratio of the leaf sample is less than the reference Mo/S ratio of a plant or of a plot not suffering from sulfur deficiency; or
the plant or the plot has a risk of sulfur deficiency and the Mo/S ratio of the leaf sample is less than the reference Mo/S ratio of a plant or of a plot suffering from sulfur deficiency, and the Mo/S ratio of the leaf sample is greater than the reference Mo/S ratio of a plant or of a plot not suffering from sulfur deficiency.

12. The method as claimed in claim 1, wherein:
the plant or the plot is suffering from sulfur deficiency and the Mo/S and (Cl+P)/S ratios of the leaf sample are respectively greater than the reference Mo/S and (Cl+P)/S ratios of a plant or of a plot suffering from sulfur deficiency;
the plant or the plot is not suffering from sulfur deficiency and the Mo/S and (Cl+P)/S ratios of the leaf sample are respectively less than the reference Mo/S and (Cl+P)/S ratios of a plant or of a plot not suffering from sulfur deficiency; or
the plant or the plot has a risk of S deficiency and the Mo/S and (Cl+P)/S ratios of the leaf sample are respectively less than the reference Mo/S and (Cl+P)/S ratios of a plant or of a plot suffering from S deficiency and respectively greater than the reference Mo/S and (Cl+P)/S ratios of a plant or of a plot not suffering from S deficiency.

13. The method as claimed in claim 1, wherein the plant or the plot is chosen from rapeseed, cabbage, tomato, corn, wheat, pea, globe amaranth, and barley.

14. The method as claimed in claim 1, wherein the plant or the plot analyzed for its sulfur nutrition state is from the same species as the plant or the plot not suffering from sulfur deficiency and/or as the plant or the plot suffering from sulfur deficiency.

15. The method as claimed in claim 1, wherein the leaf sample is dried and ground before steps b) and c).

16. The method as claimed in claim 1, wherein steps b) and c) are carried out by X-ray fluorescence spectrometry or by plasma mass spectrometry.

17. The method as claimed in claim 1, wherein steps b) and c) are carried out simultaneously.

18. The method as claimed in claim 1, wherein the plant or the plot is a plant of the species *B. napus, B. oleracea, S. lycopersicum, Z. mays, T. aestivum, P. sativum, Arabidopsis thaliana*, or *Hordeum vulgare*.

19. A method for adjusting the sulfur fertilization of a plant or of a plot, comprising the following successive steps:
A) carrying out the method of diagnosis as claimed in claim 1 on the plant or the plot; and
B) adding a sulfur-containing fertilizer if a sulfur deficiency or a risk of sulfur deficiency is detected during step A).

20. The method as claimed in claim 19, wherein a sulfur deficiency is detected when:
the Mo/S ratio of the leaf sample is greater than the reference Mo/S ratio of a plant or of a plot suffering from sulfur deficiency; and
the Mo/S and (Cl+P)/S ratios of the leaf sample are respectively greater than the reference Mo/S and (Cl+P)/S ratios of a plant or of a plot suffering from sulfur deficiency.

21. The method as claimed in claim 19, wherein a risk of sulfur deficiency is detected when:
the Mo/S ratio of the leaf sample is (i) greater than the reference Mo/S ratio of a plant or of a plot not suffering from sulfur deficiency and (ii) less than the reference Mo/S ratio of a plant or of a plot suffering from sulfur deficiency; and
the Mo/S and (Cl+P)/S ratios of the leaf sample are respectively (i) greater than the reference Mo/S and (Cl+P)/S ratios of a plant or of a plot not suffering from sulfur deficiency and (ii) less than the reference Mo/S and (Cl+P)/S ratios of a plant or of a plot suffering from sulfur deficiency.

* * * * *